United States Patent [19]
Davidson et al.

[11] 3,933,842
[45] Jan. 20, 1976

[54] 3-OXADIAZOLYL COUMARINS

[75] Inventors: Hugh Davidson, Ledston; Keith Trevor Johnson, Carleton; Brian Ernest Leggeter, Sandal; Anthony John Moore, Leeds, all of England

[73] Assignee: Hickson & Welch Limited, England

[22] Filed: Sept. 5, 1973

[21] Appl. No.: 394,494

[30] Foreign Application Priority Data
Sept. 6, 1972 United Kingdom............... 41416/72

[52] U.S. Cl.... 260/307 G; 260/45.8 NZ; 260/345.2
[51] Int. Cl.²............... C07D 271/06; C07D 271/10
[58] Field of Search.... 260/307 G, 293.58, 247.2 B, 260/295 F

[56] References Cited
UNITED STATES PATENTS
3,810,901    5/1974    Davidson et al............... 260/293.58

OTHER PUBLICATIONS

Behr– "Heterocyclic Compounds" – Vol. 17, (1962), Interscience Publishers – pp. 245–247, 263–265.

*Primary Examiner*—Raymond V. Rush
*Attorney, Agent, or Firm*—Bacon & Thomas

[57]        ABSTRACT

Substituted coumarins are described having at the 7-position the group RO- where R is a substituted or unsubstituted alkyl, cycloalkyl or aralkyl group, and at the 3-position a 1,2,4- or 1,3,4-oxadiazolyl group which possesses a substituted or unsubstituted alkyl or aryl substituent. The compounds are useful as optical whitening agents in the treatment of textile fibres.

8 Claims, No Drawings

3-OXADIAZOLYL COUMARINS

This invention is concerned with new chemical compounds of use in the whitening, brightening and/or bleaching of polyamide, polyester, polyolefin, acrylic and other synthetic materials in the form for example of textile yarns and fibres, synthetic resin sheets and the like.

Optical whitening agents have in recent years found extensive use in the treatment of textile yarns and fibres, both in their preparation and during washing, and are designed in general to counteract the yellow or off-white colour which white textiles may develop. Such optical whitening agents also tend to improve coloured textiles as they impart a general brightness to them.

The present invention is based upon the discovery of certain 3-oxadiazolyl coumarins which have particularly advantageous properties in the whitening, brightening and/or bleaching of textile fibres.

According to one feature of the invention, there are provided compounds of the general formula:

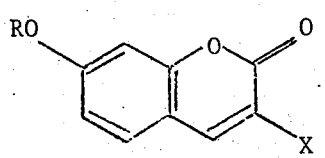

I wherein
R is an alkyl, cycloalkyl or aralkyl group, which groups may be unsubstituted or substituted by a non-chromophoric group; and
X is a 1,2,4- or 1,3,4-oxadiazolyl group of the formula:

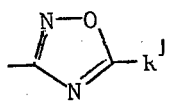  I (a)

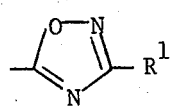  I (b)

or

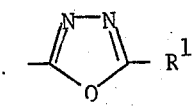  I (c)

wherein $R^1$ is an alkyl group (which may be unsubstituted or substituted by a non-chromophoric group or an aryl group) or an aryl group, which may be unsubstituted or substituted by a non-chromophoric group; and the salts of compounds of formula I which possess a basic nitrogen atom.

According to a further feature of the invention there are provided compositions for use in the treatment of an at least in part synthetic textile material comprising at least one compound of formula I as hereinbefore defined together with a solid or liquid carrier.

According to a still further feature of the invention, there is provided textile material which is at least in part synthetic having at least one compound of formula I as hereinbefore defined in association therewith.

The compounds according to the invention have especially advantageous properties in the whitening, brightening and/or bleaching of textile yarns and fibres, in particular, synthetic textile fibres (e.g. polyamide, polyolefin, acrylic and more especially polyester fibres).

The compounds according to the invention have a high thermal stability and may, if desired, be incorporated into synthetic melts, e.g. of polyester resin which may subsequently be formed into textile yarns and fibres or other shaped articles such as for example synthetic resin sheets and fibres. Where for example textile yarns and fibres are to be formed, the compounds according to the invention may be incorporated into a synthetic resin melt e.g. a polyester resin melt, and the melt then extruded to form the yarns or fibres.

The compounds according to the invention in general have a desirable violet blue fluorescence, good light fastness and good stability to chlorine-containing and oxygen bleach baths. In the tests we have carried out they have proved particularly effective in conjunction with a chlorite bleach, in that materials treated in this way show increased reflectance values.

As stated above, they in general additionally show a high degree of thermal stability and may thus be used for example in polyester resin melts for the production of textile yarns and fibres and other shaped articles as described above. They are also of course suitable for use in a more conventional manner, for example in normal dyeing processes e.g. in a dyebath at elevated temperatures and pressures, or in the pad-bake process. Solutions or dispersions of the compounds according to the invention are convenient in these processes.

In the compounds of formula I, R is preferably an alkyl group having 1-6 carbon atoms, such as methyl or ethyl, which is preferably unsubstituted but may, for example, be substituted by a non-chromophoric substituent such as a halogen, e.g. chlorine, atom. Alternatively, R may be a cycloalkyl group having for example 5-7 carbon atoms or an aralkyl group, e.g. an aralkyl group in which the aryl portion is monocyclic and the alkyl portion contains 1-6 carbon atoms, e.g. benzyl. Such groups are preferably unsubstituted, but may for example be substituted by a substituent as just referred to with reference to alkyl groups.

In the group X, $R^1$ may for example be a monocyclic aryl group such as a phenyl group, which may itself be substituted by a non-chromophoric group such as an alkyl or alkoxy group having 1-6 carbon atoms (e.g. methyl) or a halogen atom (e.g. chlorine). A further example of a substituted aryl $R^1$ group is a tetrahydronaphthyl group. $R^1$ may alternatively be an alkyl group having for example 1-6 carbon atoms (e.g. methyl) which may be substituted by a non-chromophoric group such as a halogen (e.g. chlorine) atom or an aryl group such as referred to above (e.g. phenyl).

Where $R^1$ is an alkyl group it may also be substituted by a dialkylamino group (e.g. in which the alkyl groups have 1-6 carbon atoms) or the N-attached residue of a nitrogen containing heterocyclic ring. The heterocyclic ring may for example be a monocyclic saturated 5- or 6-membered ring which may contain a further ring hetero atom such as O, N or S (e.g. a piperidino or morpholino group). The heterocyclic ring may alternatively be aromatic, e.g. a 5- or 6-membered monocylic group such as pyridinium; an anion such as a halide ion will of course be associated with such a group. Compounds wherein $R^1$ contains a basic nitrogen atom are capable of forming salts with acids or quaternary salts, and such salts are also included within the scope of the invention.

X is preferably a 1,2,4-oxadiazol-5-yl derivative.

It will be appreciated that non-chromophoric substituents such as referred to above may be present at other positions in the molecule.

Particularly preferred compounds in accordance with the invention on account of their especially advantageous whitening, brightening and/or bleaching properties are:

7-ethoxy-3-(3-phenyl-1,2,4-oxadiazol-5-yl)-coumarin;

7-ethoxy-3-[3-(p-tolyl)-1,2,4-oxadiazol-5-yl]-coumarin;

7-methoxy-3-(3-methyl-1,2,4-oxadiazol-5-yl)-coumarin; and 7-methoxy-3-(3-benzyl-1,2,4-oxadiazol-5-yl)-coumarin.

For the purpose of treating previously-formed textile yarns and fibres in general, the compounds according to the invention may be incorporated into compositions comprising at least one compound of formula I together with a solid or liquid carrier. Such compositions may for example be adapted for use in the washing of finished polyamide, polyolefin, polyester and acrylic fibres and can take the form of solutions, suspensions and dispersions of compounds of formula I in appropriate liquid carriers such as water, sulpholane, dimethylformamide and dimethylsulphoxide. When dispersions are used they conveniently include dispersing agents such as for example alkyl naphthalene sulphonates. Aqueous compositions may, if desired, also contain, for example, synthetic detergents, soaps or surface active agents. Alternatively the compositions may be in solid form and comprise at least one compound according to the invention together with a solid synthetic detergent or soap as carrier. The compounds of formula I may be employed in the manufacture of synthetic yarns and fibres, e.g. by addition to compositions from which the fibres are prepared by spinning or extrusion.

The compounds of the invention may be prepared by any convenient route and are advantageously prepared by one of the following processes.

Compounds of formula I wherein X is a group of the formula I (a) may be prepared by reacting an appropriately substituted coumarin having a 3-amidoximino group with a functional derivative of a carboxylic acid of the formula $R^1COOH$ where $R^1$ is as defined above. The starting coumarin may be regarded as a compound of formula I wherein X is the group:

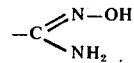

and may be prepared for example by reacting the corresponding 3-cyano coumarin with hydroxylamine. The functional derivative of the carboxylic acid may for example be an acid halide (preferably the chloride), or anhydride or an ester (e.g. a $C_{1-6}$ alkyl ester).

The reaction may for example be carried out at an elevated temperature (e.g. above 100°C) with an acid halide which also functions as the reaction solvent.

Compounds of formula I wherein X is a group of the formula I (b) may be prepared by reacting a functional derivative of an appropriately substituted coumarin-3-carboxylic acid (i.e. a compound of formula I wherein X is a carboxylic acid group) with an amidoxime of the formula

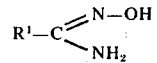

where $R^1$ is as defined above. The functional derivative of the carboxylic acid may be an acid halide (preferably the chloride), or anhydride or an ester. The reaction is conveniently carried out by first reacting the two reagents in a ketone solvent such as acetone at ambient temperatures, and thereafter refluxing the intermediate so formed in a hydrocarbon solvent such as decahydronaphthalene in the presence of an acid catalyst (e.g. boric acid).

Compounds of the formula I wherein X is a group of the formula I (c) may be prepared by the cyclisation of an appropriately substituted acid hydrazide, i.e. a compound of formula I wherein X is the group —CO.NH.NH.CO.$R^1$ where $R^1$ is as defined above. This reaction may be effected in an inert polar solvent such as dimethylformamide with a dehydrating agent such as thionyl chloride, conveniently at reflux.

The acid hydrazide starting materials required for this reaction may be prepared by reacting a functional derivative of a coumarin-3-carboxylic acid, such as referred to above, with hydrazine of the formula $H_2N.NH.CO.R^1$.

The following examples illustrate the invention.

EXAMPLE 1

2.5 parts 7-ethoxy coumarin-3-carbonyl chloride and 1.4 parts of benzamidoxime were stirred in 25 parts of acetone at room temperature for 30 mins. and then refluxed for a further 30 mins., the mixture cooled and the resultant pale cream solid collected, washed with acetone and dried. This intermediate was added to 25 parts of boiling decahydronaphthalene containing 0.1 parts boric acid. After refluxing for 1½ hours the reaction mixture was cooled and the solid filtered off and recrystallised from cellosolve. The yield of 1.7 parts of 3-(3-phenyl-1,2,4-oxadiazol-5-yl)-7-ethoxy coumarin melted at 233°C and has an $E_1^1$ of 930 at 368 m$\mu$.

Analysis: calculated for $C_{19}H_{14}N_2O_4$: C 68.3, H 4.2, N 8.4; found C 68.2, H 4.2, N 8.7.

EXAMPLE 2

Example 1 was repeated with 1.5 parts of p-toluamidoxime replacing the benzamidoxime. The resultant 1.7 parts of 3-[3-(p-tolyl)-1,2,4-oxadiazol-5-yl]-7-ethoxy coumarin had a melting point of 228°C and an $E_1^1$ of 880 at 368 m$\mu$. Analysis: calculated for $C_{20}H_{16}N_2O_4$: C 69.0, H 4.6, N 8.0; found: C 68.7, H 4.6, N 8.4.

EXAMPLE 3

4.0 parts 3-cyano-7-methoxycoumarin in 40 parts of n-butanol were mixed with 3 parts of hydroxylamine hydrochloride and 2 parts of potassium carbonate in 30 parts of water. The resultant mixture was refluxed for 3 hours and the orange solution precipitated 2.3 parts of 3-amidoximino-7-methoxycoumarin, M.P. 192°–6°C.

2.3. parts of 3-amidoximino-7-methoxycoumarin and 5 parts chloracetyl chloride were heated at 130° for 30 mins. The reaction mixture was poured into water and the solid collected and recrystallised from ethanol. The yield of 3-(5-chloromethyl-1,2,4-oxadiazol-3-yl)-7-methoxycoumarin was 2 parts, M.P. 187.5°C.

EXAMPLE 4

2.3 parts of 3-amidoximino-7-methoxycoumarin and 10 parts of acetic anhydride were refluxed for 10 hours and then poured into water. The solid was collected washed with water and recrystallised from cellosolve to give 2 parts of 3-(5-methyl-1,2,4-oxadiazol-3-yl)-7-methoxycoumarin, M.P. 218°–20°C, $E_1^1$ 910 at 348 mμ. Analysis: calculated for $C_{13}H_{10}N_2O_4$: C 60.5, H 3.9, N 10.8; found C 60.1, H 4.0, N 10.5.

EXAMPLE 5

The following oxadiazolyl coumarins were prepared by methods analogous to that of Example 1.

7-Methoxy-3-(3-phenyl-1,2,4-oxadiazol-5-yl)coumarin

M.pt. 216°C. $E_1^1$ 940 at 366 mμ.

Calculated for $C_{18}H_{12}N_2O_4$ C 67.5 H 3.8 N 8.7 MeO 9.7. Found C 67.4 H 3.9 N 8.6 MeO 9.8.

7-Methoxy-3-(3(p-tolyl)-1,2,4-oxadiazol-5-yl)coumarin

M.pt. 231°C. $E_1^1$ 870 at 366 mμ.

Calculated for $C_{19}H_{24}N_2O_4$ C 68.3 H 4.2 N 8.4 MeO 9.3. Found C 68.3 H 4.4 N 8.4 MeO 9.2.

7-Methoxy-3-(3-(3(p-methoxyphenyl)-1,2,4-oxadiazol-5-yl)coumarin

M.pt 230°C. $E_1^1$ 850 at 366 mμ.

Calculated for $C_{20}H_{16}N_2O_5$ C 65.1 H 4.0 N 8.0 Meo 17.7. Found C 65.3 H 4.5 N 8.1 MeO 17.5.

7-Methoxy-3-(3-methyl-1,2,4-oxadiazol-5-yl)coumarin

M.pt. 201°C. $E_1^1$ 950 at 364 mμ.

Calculated for $C_{13}H_{10}N_2O_4$ C 60.5 H 3.9 N 10.8 MeO 12.0. Found C 60.5 H 4.4 N 10.6 MeO 12.2.

3-(3-Benzyl-1,2,4-oxadiazol-5-yl)-7-methoxycoumarin

M.pt. 168°C. $E_1^1$ 840 at 364 mμ.

Calculated for $C_{19}H_{14}N_2O_4$ C 68.3 H 4.2 N 8.4. Found C 68.3 H 4.4 N 8.3.

EXAMPLE 6

The following compounds were prepared by methods analogous to that of Example 1:

7-Ethoxy-3(3-(p-methoxyphenyl)-1,2,4-oxadiazol-5-yl)coumarin

M.pt 222°C $E_1^1$ 910 at 366–7 mμ.

Calculated for $C_{21}H_{18}N_2O_5$ C 65.9 H 4.4. N 7.7. Found C 66.1 H 4.7 N 7.5.

7-Ethoxy-3(3-methyl-1,2,4-oxadiazol-5-yl)coumarin
M.pt. 155°C $E_1^1$ 970 at 365–6 mμ.

Calculated for $C_{14}H_{12}N_2O_4$ C 61.8 H 4.4 N 10.3. Found C 61.8 H 4.8 N 10.0.

3-(3-Benzyl-1,2,4-oxadiazol-5-yl)-7-ethoxy coumarin

M.pt. 177°C $E_1^1$ 860 at 366–7 mμ.

Calculated for $C_{20}H_{16}N_2O_4$ C 69.0 H 4.6 N 8.0. Found C 69.3 H 5.0 N 7.8.

3-(3-(p-Chlorophenyl)-1,2,4-oxadiazol-5yl)-7-methoxy coumarin

M.pt over 300°C. $E_1^1$ 830 at 364 mμ.

Calculated for $C_{18}H_{11}N_2O_4Cl$ C 60.9 H 3.1 N 7.9 Cl 10.0. Found C 61.2 H 3.1 N 7.9 Cl 9.9.

7-Benzyloxy-3-(3-phenyl-1,2,4-oxadiazol-5-yl)coumarin

M.pt. 227°C.

7-Benzyloxy-3-(3-chloromethyl-1,2,4-oxadiazol-5-yl)coumarin

M.pt. 190°C.

7-Benzyloxy-3-(dibutylaminomethyl-1,2,4-oxadiazol-5-yl)coumarin

M.pt. 160°C.

3-(3-Chloromethyl-1,2,4-oxadiazol-5-yl)-7-methoxy coumarin

M.pt. 172°C.

3-(3-(1,2,3,4-tetrahydronaphth-6-yl)1,2,4-oxadiazol-5-yl)-7-benzyloxy coumarin

M.pt. 214°–216°C. $E_1^1$ 696 at λmax. 367 mμ.

3-(3-(1,2,3,4-tetrahydronaphtha-6-yl) 1,2,4-oxadiazol-5-yl)-7-methoxy coumarin

M.pt. 235°C. $E_1^1$ 800 at λmax. 364 mμ.

5-(7-Benzyloxycoumarin-3-yl)-1,2,4-oxadiazol-3-yl-methylpyridinium chloride

M.pt. 260°–2°C.

5-(7-methoxycoumarin-3-yl)-1,2,4-oxadiazol-3-yl methyl pyridinium chloride

M.pt. 231°C. $E_1^1$ 722 at 367 mμ.

EXAMPLE 7

4.8 Parts of 7-methoxycoumarin-3-carbonyl chloride and 2.8 parts of N-benzoylhydrazine were refluxed in 35 parts of chlorobenzene with stirring until no further hydrogen chloride was evolved. The mixture was refluxed for a further 30 minutes, cooled, and the solid collected to afford 6.5 parts of a diacylhydrazine of formula:

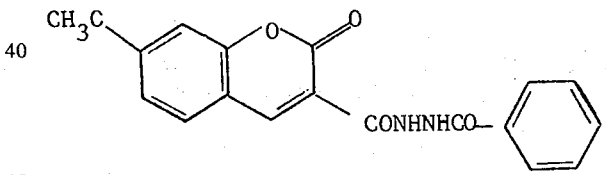

4.3 Parts of this latter compound in 20 parts of dimethylformamide were heated to 110°C and 5 parts of thionyl chloride were added dropwise. The resultant mixture was heated until a clear solution was obtained, and then cooled. The crystallized solid was collected, recrystallised from dimethylformamide and isolated to yield 1.5 parts of 7-methoxy-3-(5-phenyl-1,3,4-oxadiazol-2-yl)coumarin. The product melted at 253°–4° and imparted a vivid blue fluorescence to its solution in acetone.

$E_1^1$ 930 at λmax. 366 mμ.

Analysis calcuated for $C_{18}H_{12}N_2O_4$ C: 72.7% H: 4.1% N: 7.1%. Found C: 72.2% H: 4.4% N: 7.1%.

EXAMPLE 8

The following compound was prepared by a method analogous to that of Example 8:

7-Benzyloxy-3-(5-phenyl-1,3,4-oxadiazol-2-yl) coumarin

M.pt. 255°C. $E_1^1$ 785 at 366 mμ.

Analysis calculated for $C_{24}H_{16}N_2O_4$ C: 67.5% H: 3.8% N: 8.7%. Found C: 66.8% H: 4.1% N: 8.8%.

EXAMPLE 9

Fibres of polyester are introduced in a liquor ratio of 1:40 into a bath containing 1 g./l. sodium oleyl sulphate, 0.75 g./l. formic acid and 0.1 g./l. the compound of Example 1. The bath is heated at the boil for 30 minutes and the fibres rinsed and dried. Compared with the untreated material the polyester exhibits a much whiter and brighter effect which is fast to light, washing and chlorite.

We claim:

1. A compound of the formula:

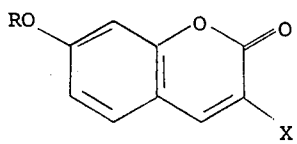

[I]

wherein R is $C_1$-$C_6$ alkyl, $C_5$-$C_7$ cycloalkyl or phenyl alkyl in which the alkyl moiety is of 1 to 6 carbon atoms or any of these groups substituted by a non-chromophoric group; and X is a 1,2,4- or 1,3,4-oxadiazolyl group of the formula:

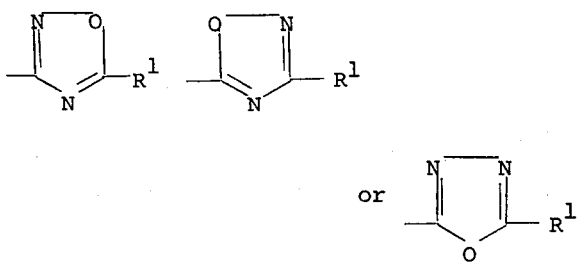

wherein $R^1$ is $C_1$-$C_6$ alkyl; $C_1$-$C_6$ alkyl substituted by a nonchromophoric group; phenyl or phenyl substituted by a non-chromophoric group; or when said compound possesses a basic nitrogen atom a salt thereof with an acid or a quaternary salt thereof wherein said acid or quaternary salt are non-chromophoric.

2. A compound as claimed in claim 1 in which R is $C_1$-$C_6$ alkyl, $C_5$-$C_7$ cycloalkyl or phenalkyl in which the alkyl moiety is of 1 to 6 carbon atoms or any of these groups substituted by halo and $R^1$ is phenyl; phenyl substituted by $C_1$-$C_6$ alkyl, $C_1$-$C_6$ alkoxy or halo; tetrahydronaphthyl; $C_1$-$C_6$ alkyl; or $C_1$-$C_6$ alkyl substituted by halo, phenyl, di ($C_1$-$C_6$) alkylamino or N-attached piperidino, morpholino or pyridinium, and when said N-attached group is pyridinium, a non-chromophoric anion.

3. A compound as claimed in claim 1 wherein X is

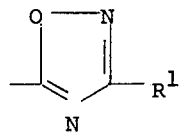

4. A compound as claimed in claim 1 wherein R is $C_1$-$C_6$ alkyl or $C_5$-$C_7$ cycloalkyl.

5. A compound as claimed in claim 1 wherein R is methyl or ethyl.

6. A compound as claimed in claim 4 wherein $R^1$ is phenyl; phenyl substituted by $C_1$-$C_6$ alkyl, $C_1$-$C_6$ alkoxy or a halogen atom; $C_1$-$C_6$ alkyl; or $C_1$-$C_6$ alkyl substituted by a halogen atom or phenyl.

7. A compound as claimed in claim 1 wherein $R^1$ is $C_1$-$C_6$ alkyl substituted by di ($C_1$-$C_6$) alkylamino or N-attached piperidino, morpholino or pyridinium; or tetrahydronaphthyl.

8. A compound as claimed in claim 1 which is 7-ethoxy-3-(3-phenyl-1,2,4-oxadiazol-5-yl)-coumarin; 7-ethoxy-3-[3-(p-tolyl)-1,2,4-oxadiazol-5-yl]-coumarin; 7-methoxy-3-(3-methyl-1,2,4-oxadiazol-5-yl)-coumarin; or 7-methoxy-3-(3-benzyl-1,2,4-oxadiazol-5-yl)-coumarin.

* * * * *